United States Patent [19]

Wang et al.

[11] Patent Number: 4,492,762

[45] Date of Patent: Jan. 8, 1985

[54] FLUORESCENT POLARIZATION IMMUNOASSAYS

[75] Inventors: Chao-Huei J. Wang, Gurnee; Stephen D. Stroupe, Libertyville; Michael E. Jolley, Round Lake, all of Ill.

[73] Assignee: Abbott Laboratories, North Chicago, Ill.

[21] Appl. No.: 393,577

[22] Filed: Jun. 30, 1982

Related U.S. Application Data

[63] Continuation-in-part of Ser. No. 329,974, Dec. 11, 1981, which is a continuation-in-part of Ser. No. 235,259, Feb. 17, 1981, abandoned, Ser. No. 329,975, Dec. 11, 1981, and Ser. No. 325,872, Nov. 30, 1981, Pat. No. 4,420,568, said Ser. No. 325,872, is a continuation of Ser. No. 173,553, Jul. 30, 1980, abandoned.

[51] Int. Cl.³ ............................................. G01N 33/54
[52] U.S. Cl. .................................... 436/537; 436/536; 436/800; 436/825
[58] Field of Search ................. 436/518, 800, 825, 97, 436/536, 537

[56] References Cited

U.S. PATENT DOCUMENTS

| 4,115,699 | 9/1978 | Mizuta et al. | 250/461.2 |
| 4,204,839 | 5/1980 | Wu et al. | 436/97 X |
| 4,252,783 | 2/1981 | Kam et al. | 436/825 |

Primary Examiner—Arnold Turk
Attorney, Agent, or Firm—James L. Wilcox

[57] ABSTRACT

Improvement in fluorescent polarization immunoassays for substances in blood plasma or serum comprising conducting the assays in dilute anionic surfactant solutions which disrupt the fluorescent bilirubin serum albumin complex without disturbing the antibody reaction in the immunoassay. In this manner, background fluorescence in icteric samples is greatly reduced.

4 Claims, No Drawings

FLUORESCENT POLARIZATION IMMUNOASSAYS

BACKGROUND OF THE INVENTION

This is a continuation-in-part of U.S. patent application Ser. No. 329,974, filed Dec. 11, 1981, which is a continuation-in-part of Ser. No. 06/235,259 filed Feb. 17, 1981, now abandoned; Ser. No. 329,975, filed Dec. 11, 1981; and Ser. No. 325,872, filed Nov. 30, 1981, now U.S. Pat. No. 4,420,568 which is a continuation of Ser. No. 06/173,553 filed July 30, 1980, now abandoned.

Fluorescence polarization immunoassay (FPIA) has been developed into a useful clinical tool by Abbott Diagnostics Division. FPIA's have been developed which measure the concentration of gentamicin, tobramycin, amikacin, kanamycin, phenytoin, phenobarbital, valproic acid, carbamazepine, theophylline, methotrexate, lidocaine, imipramine, and amitriptylene, among other compounds, in body fluids such as serum, plasma, saliva, or urine. In these assays, a small volume of the fluid to be assayed is mixed with a fluorescent derivative of the compound to be measured followed by the addition of an antiserum specific for the compound under investigation. After an incubation period, the fluorescence polarization of the solution is read. The polarization of the sample reflects the degree of tracer binding to the antiserum and in turn reflects the concentration of of analyte in the sample in a simple competitive binding manner.

The expression for polarization is:

$P = (I_v - I_h)/(I_v + I_h)$ where $I_v$ is the fluorescence intensity when the analyzer polarizer is vertically oriented, and $I_h$ was the analyzer in the horizontal position. Ideally the only source of fluorescence in the solution should be the fluorescent derivative of the analyte. In practice there are several sources of fluorescence intensity which contribute to the overall fluorescence polarization; the major sources being the fluorescent tracer, the buffer, and the sample.

If the composition of the reaction mixture is well controlled, the fluorescence contribution of the individual samples will be the only variable between samples.

$$P = \frac{I_v^{Tracer+Buffer} + I_v^{Sample} - (I_h^{Tracer+Buffer} + I_h^{Sample})}{I_v^{Tracer+Buffer} + I_v^{Sample} + I_h^{Tracer+Buffer} + I_h^{Sample}}$$

For example, a sample of a P of 0.5 and a vertical intensity of 0.3 volts will introduce an error of 0.0195 into the determination of a polarization reading of 0.125 with a vertical intensity due to Tracer and Buffer of 4.5 volts.

$$P\ true = \frac{4.5 - 3.5}{4.5 + 3.5} = \frac{1}{8} = 0.125$$

$$P\ apparent = \frac{4.5 + 0.3 - (3.5 + 0.1)}{4.8 + 3.6} = \frac{1.2}{8.3} = 0.1445$$

Therefore, to reduce errors in polarization readings it is necessary to minimize the fluorescence contribution of the sample.

Icteric serum or plasma can contribute a significant error to the desired polarization measurement. A major fluorescent component of icteric serum is albumin-bound bilirubin. Bilirubin is the final product of heme catabolism and in normal individuals is present in serum at less than 1 mg/dl. In various disease states affecting the liver, bilirubin is markedly elevated, reaching 10-20 mg/dl in some cases. Neonates often attain high levels in the 10-20 mg/dl range due to poor liver function immediately post-partum. Bilirubin is nonfluorescent when it is in aqueous solution, but it becomes weakly fluorescent if bound to albumin [Chen, R. F. (1974) Arch. Biochem. Biophys. 160 106–112] and bilirubin-albumin binding is very tight [Gray, R. D., and Stroupe, S. D. (1978) J. Biol. Chem. 253 4370–4377]. Therefore, serum or plasma samples with elevated bilirubin levels will exhibit an elevated fluorescence due to the presence of the bilirubin-albumin complex.

SUMMARY OF THE INVENTION

This invention involves a method for reducing background fluorescence in fluorescence polarization immunoassays. The principal cause of such fluorescence is the bilirubin-albumin complex and this invention describes a method for dissociating the complex without disturbing the antibody-hapten reaction used to measure the analyte. It has been discovered that anionic surfactants in the concentration range of about 0.001-0.1% (weight/volume) range are very effective for this purpose.

DETAILED DESCRIPTION OF THE INVENTION

It has been discovered that intrinsic fluorescence in icteric serum and plasma samples can be significantly reduced by the addition of dilute solutions of anionic surfactants. This intrinsic background fluorescence is very undesirable in fluorescence polarization immunoassays and the reduction of intrinsic fluorescence, especially fluorescence due to bilirubin albumin complex, is essential for proper conducting of such assays.

Dilute solutions of anionic surfactants, when used as diluents for fluorescent polarization reagents, provides effective results.

Anionic surfactants such as:

(1) Ammonium, lithium, and sodium salts of alkyl sulfates of the formula $CH_3(CH_2)_n\text{-}OSO_3^{\ominus}M^+$ where $n = 5\text{-}15$ and $M = NH_4^+$, $Li^+$, or $Na^+$. Sodium dodecyl sulfate is particularly effective ($n = 11$).

(2) Salts of alkyl benzene sulfonates of the formula

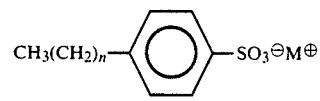

$n = 0$ to $11$, $M = NH_4^+$, $Li^+$, $Na^+$.

(3) Salts of bile acids such as sodium cholate or sodium deoxycholate.

(4) Salts of mono or di carboxylic acids which have the structure

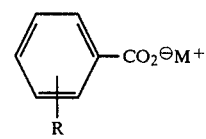

where $R = COO^-M^{\oplus}$ or $-OH$ and $M^+ = NH_4^+$, $Na^+$, $Li^+$.

Sodium dodecyl sulfate, sodium toluene sulfonate, and sodium cholate are preferred. Concentration ranges of 0.001 to 0.2 (weight/volume) percent are preferred. Sodium dodecyl sulfate in a concentration range of 0.001–0.02% weight/volume percent is a most preferred reagent.

Table I summarizes the reduction in fluorescence by sodium dodecyl sulfate (SDS) for a series of icteric samples compared to a normal human serum pool.

TABLE I

| Sample | Bilirubin (mg/dl) | Fluorescence Intensity containing | |
|---|---|---|---|
| | | 0% SDS | 0.01% SDS |
| 245 | 13.4 | 327 | 150 |
| 246 | 13.4 | 379 | 138 |
| 237 | 15.0 | 408 | 173 |
| 247 | 15.2 | 482 | 172 |
| 7 | 6.0 | 313 | 100 |
| 221 | 4.7 | 190 | 88 |
| 229 | 2.1 | 139 | 96 |
| 230 | 2.4 | 107 | 64 |
| 233 | 6.8 | 202 | 98 |
| NHS | 0.2 | 50 | 49 |

A typical assay for gentamicin is as follows: Materials Required:

(1) Buffer: 0.1M phosphate, pH 7.5, containing 0.01% bovine gamma globulin (BGG buffer).

(2) Tracer: Gentamicin-DTAF at 100 nM in a tris-hydrochloride buffer pH 7.5 containing 0.125% sodium dodecyl sulfate, 0.01% sodium azide, and 0.01% bovine gamma globulin.

(3) Antibody: Rabbit or sheep antisera to gentamicin diluted approximately in buffer.

(4) Standards or unknowns: human serum (or other biological fluid) containing gentamicin.

(5) Fluorescence polarimeter: An instrument capable of reading fluorescence polarization with a precision of ±0.001 units.

Protocol:

(1) 1.8 μl of standard of unknown sample is placed in a 12×75 mm disposable culture tube (cuvette). This is done by pipetting 20 μl of sample followed by 200 μl of buffer. Next 20 μl of diluted sample is pipetted into the cuvette followed by 200 μl of buffer.

(2) 40 μl of tracer and 1000 μl of buffer are added to the cuvette.

(3) 40 μl of antibody and 1000 μl of buffer are added, the contents of the cuvette are mixed and incubated for approximately fifteen minutes at room temperature.

(4) The fluorescence polarization is read following the incubation. Typical results are presented in Table II.

TABLE II

| Gentamicin Concentration (ug/ml) | Polarization |
|---|---|
| 0 | 0.178 |
| 0.5 | 0.158 |
| 1.0 | 0.140 |
| 2.0 | 0.115 |
| 4.0 | 0.090 |
| 8.0 | 0.074 |

The polarization changes in a regular manner allowing construction of s standard curve. Unknown samples are tested in an identical manner, and the gentamicin content is determined by reference to the standard curve.

Preparation of the gentamicin-DTAF complex is described in Example 1. The hereinafter examples further illustrate the invention and should not be construed to limit the invention in spirit or scope.

EXAMPLE 1

Gentamicin sulfate (200 mg) was dissolved in 1 ml of distilled water and the resulting solution was adjusted to pH 9.0 using approximately 0.8 ml of 1.0M sodium hydroxide. 5-[4,6-dichlorotriazin-2-yl)amino]fluorescein (20 mg) was dissolved in 1.5 ml of methanol and the resulting methanol solution was added dropwise to the gentamicin solution with stirring. The reaction mixture was allowed to react for one hour. The resultant mixture was chromatographed on a DEAE cellulose medium mesh column using 0.1M phosphate buffer at pH 8.0 as the eluent to yield a gentamicin-DTAF conjugate.

EXAMPLE 2

Meta- or para-aminophenobarbital (5 mg) and carboxyfluorescein (5 mg) were dissolved in 0.5 ml of pyridine. To the mixture was added N,N'-dichohexylcarbodiimide (15 mg). The reaction proceeded for two hours at room temperature, after which time the reaction product was purified twice employing silica gel thin-layer chromatography using a chloroform:methanol (2:1) mixture as developing solvent to yield an aminophenobarbital-carboxyfluorescein [CF] conjugate of the formula:

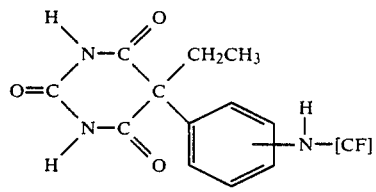

A. Materials required:

(1) BGG buffer (2) Tracer, consisting of aminophenobarbital carboxyfluorescein at a concentration of approximately 110 nM in this HCl buffer, pH 7.5, containing 0.01% sodium azide, 0.01% bovine gamma globulin (BGG) and 0.125% sodium dodecyl sulfate.

(3) Antiserum, consisting of antiserum against phenobarbital diluted appropriately in BGG buffer containing 0.005% benzalkonium chloride.

(4) Samples of human serum or other biological fluid containing phenobarbital.

(5) Cuvettes (12×75 mm culture tubes).

(6) Fluorometer (capable of reading fluorescence polarization with a precision of ±0.001 units).

B. Assay Protocol:

(1) A small volume of sample (0.196 microliter) is placed in the cuvette by pipetting 10 μl of sample and diluting with 500 μl BGG buffer in a dilution vessel. Next, 10 μl of diluted sample is pipetted into the cuvette followed by 500 μl BGG buffer.

(2) Tracer is added by pipetting 40 μl of tracer and 1000 μl BGG buffer into each cuvette.

(3) Antiserum is added to start the reaction by pipetting 40 μl antiserum followed by 1000 μl BGG buffer.

(4) The contents of all cuvettes are mixed well and allowed to incubate for 15 minutes at ambient temperature.

(5) The fluorescence polarization is read on a fluorometer and a standard curve constructed to determine unknowns.

C. The results of a series of serum standards containing phenobarbital at concentrations between 0 and 80 μg/ml are presented below. Each concentration was assayed in duplicate and the values averaged.

| Concentration of Phenobarbital (ul) | Polarization |
| --- | --- |
| 0 | 0.250 |
| 5.0 | 0.231 |
| 10.0 | 0.196 |
| 20.0 | 0.150 |
| 40.0 | 0.104 |
| 80.0 | 0.077 |

The polarization of fluorescence is seen to decrease in a regular manner as the phenobarbital concentration increases, allowing construction of a standard curve. Unknown specimens treated in an identical manner can be quantitated by reference to the standard curve.

EXAMPLE 3

To a solution containing 2 g. of iminostilbene and 2 ml. of triethylamine in 50 ml. of chloroform was added 1.5 g. of methyloxyalylchloride. The resultant mixture was refluxed for one hour and then evaporated to dryness. The residue was taken up in 50 ml. of chloroform and then extracted with 50 ml. of water. The chloroform layer was evaporated to dryness. To the residue was added 100 ml. of 2N sodium hydroxide and the resultant mixture was refluxed for 30 minutes. The mixture was cooled to room temperature and then extracted with 50 ml. of chloroform. The aqueous layer was acidified to pH 1 using concentrated hydrochloric acid and then extracted with 100 ml. of ether. The organic extract was dried over sodium sulfate and evaporated to dryness. The residue was taken up in 50 ml. of methanol and triturated with water to yield a crop of crystals. The mixture was filtered and the crystals were cooled for 16 hours to yield 2.4 g. of a N-hydroxyoxalyl-iminostilbene (m.p. 162°–163° C.).

To 5 mg. of the N-hydroxyoxalyl-iminostilbene was added a solution containing 5 mg. of 4-aminofluorescein in 0.5 ml. of pyridine. The reaction was allowed to proceed for two hours at 26° C. to yield a crude product. The crude product was purified using thin-layer chromatography employing silica gel and a developing solution consisting of a mixture of chloroform:acetone (1:1) to yield an N-oxalyl-iminostilbene-aminofluorescein [AF] conjugate of the formula:

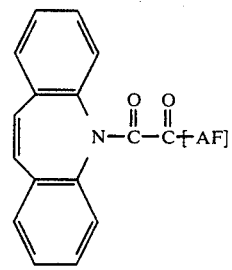

Materials (1) BGG buffer.
(2) Tracer solution (N-oxalyl-iminostilbene-aminofluorescein) in BGG buffer containing 5.76% (weight volume) sodium toluene sulfonate. Concentration of tracer = 0.17μ molar.
(3) Antibody: SHeep antiserum to carbamazepine diluted 1 to 40 in BGG buffer.
(4) Standards or unknowns: Human serum (or other biological fluid) containing carbamazepine in a concentration range of 0 to 20 μg/ml.
(5) Fluorescence polarimeter: Instrument capable of measuring the polarization of fluorescence of $1 \times 10^{-9}$M fluorescence solution to ±0.001 polarization units.

Protocol (1) To 25 μl of standards and unknowns add 600 μl of BGG buffer.
(2) To 25 μl of each diluted standard and unknown in a culture tube add 600 μl of BGG buffer.
(3) Add 40 μl of tracer to each culture tube, followed by 800 ml BGG buffer.
(4) Then add 40 μl of antibody to each culture tube followed by 800 ml BGG buffer.
(5) Mix the reagents and incubate the culture tubes containing standards and unknowns for approximately 15 minutes at room temperature.
(6) Measure the fluorescence polarization of all tubes. Typical results for standard samples are presented in Table III.

TABLE III

| Carbamazepine Concentration (ug/ml) | Polarization |
| --- | --- |
| 0 | 0.289 |
| 2 | 0.253 |
| 4 | 0.218 |
| 8 | 0.188 |
| 12 | 0.164 |
| 20 | 0.137 |

The polarization values decrease as the concentration of carbamazepine is increased, allowing construction of a standard curve. Unknowns treated in an identical manner may be quantitated by reference to the standard curve.

What is claimed is:

1. In a fluorescent polarization immunoassay for a substance in blood serum or plasma the improvement comprising:
    conducting the fluorescent polarization immunoassay in a solution containing effective amounts of an anionic surfactant to disrupt bilirubin serum albumin complex in the sample and thereby reduce background fluorescence of the blood serum or plasma sample.
2. The improvement according to claim 1 wherein the anionic detergent is sodium dodecyl sulfate.
3. The improvement according to claim 1 wherein the anionic detergent is sodium cholate.
4. The improvement according to claim 1 wherein the detergent is sodium toluene sulfonate.

* * * * *

REEXAMINATION CERTIFICATE (1529th)
United States Patent [19]
Wang et al.

[11] B1 4,492,762

[45] Certificate Issued Aug. 13, 1991

[54] FLUORESCENT POLARIZATION IMMUNOASSAYS

[75] Inventors: Chao-Huei J. Wang, Gurnee; Stephen D. Stroupe, Libertyville; Michael E. Jolley, Round Lake, all of Ill.

[73] Assignee: Abbott Laboratories, Abbott Park, Ill.

Reexamination Reqs:st:
No. 90/001,162, Feb. 6, 1987
No. 90/001,314, Aug. 25, 1987
No. 90/001,614, Oct. 5, 1988

Reexamination Certificate for:
Patent No.: 4,492,762
Issued: Jan. 8, 1985
Appl. No.: 393,577
Filed: Jun. 30, 1982

Related U.S. Application Data

[63] Continuation-in-part of Ser. No. 329,974, Dec. 11, 1981, which is a continuation-in-part of Ser. No. 235,259, Feb. 17, 1981, abandoned, Ser. No. 329,975, Dec. 11, 1981, and Ser. No. 325,872, Nov. 30, 1981, Pat. No. 4,420,568, said Ser. No. 325,872, is a continuation of Ser. No. 173,553, Jul. 30, 1980, abandoned.

[51] Int. Cl.$^5$ .......................................... G01N 33/542
[52] U.S. Cl. .................................... 436/537; 436/536; 436/800; 436/825

[56] References Cited

U.S. PATENT DOCUMENTS

4,292,041  9/1981  Fullerton ............................... 436/86

OTHER PUBLICATIONS

Kobayashi et al; Steroids, vol. 34, No. 7, pp. 829–834 (Dec. 1979).
Novros et al; Clin. Chem. vol. 25, No. 11, pp. 1891–1899 (1979).
Westwood: Anal. Clin. Biochem., vol. 19, pp. 151–156 (1982).

*Primary Examiner*—Robert J. Hill, Jr.

[57] ABSTRACT

Improvement in fluorescent polarization immunoassays for substances in blood plasma or serum comprising conducting the assays in dilute anionic surfactant solutions which disrupt the fluorescent bilirubin serum albumin complex without disturbing the antibody reaction in the immunoassay. In this manner, background fluorescence in icteric samples is greatly reduced.

B1 4,492,762

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-4, dependent on an amended claim, are determined to be patentable.

1. In a fluorescent polarization immunoassay for a substance in *a* blood serum or plasma *sample*, the improvement comprising:

adding to a solution comprising the sample, an amount within the range of 0.001 to 0.2% (weight/volume) of an anionic surfactant and conducting the fluorescent polarization immunoassay in [a] *said* solution containing [effective amounts of] *said amount of* [an] *said* anionic surfactant to disrupt bilirubin serum albumin complex in the sample and thereby reduce background fluorescence of the blood serum or plasma sample.

* * * * *